United States Patent
Abe (10) Patent No.: US 10,021,293 B2
(45) Date of Patent: Jul. 10, 2018

(54) IMAGE CAPTURE APPARATUS, IMAGE CAPTURE PROCESSING SYSTEM AND METHOD FOR PROCESSING IMAGE CAPTURE

(71) Applicant: CANON KABUSHIKI KAISHA, Tokyo (JP)

(72) Inventor: Ken-ichi Abe, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/135,365

(22) Filed: Dec. 19, 2013

(65) Prior Publication Data
US 2014/0176772 A1 Jun. 26, 2014

(30) Foreign Application Priority Data
Dec. 21, 2012 (JP) .................... 2012-279484

(51) Int. Cl.
| | | |
|---|---|---|
| H04N 5/222 | (2006.01) | |
| H04N 5/232 | (2006.01) | |
| G06Q 50/22 | (2018.01) | |
| G06F 19/00 | (2018.01) | |
| G16H 40/63 | (2018.01) | |

(52) U.S. Cl.
CPC ....... *H04N 5/23222* (2013.01); *G06F 19/321* (2013.01); *G06Q 50/22* (2013.01); *G16H 40/63* (2018.01); *H04N 5/23203* (2013.01)

(58) Field of Classification Search
CPC ............ H04N 5/23222; H04N 5/23203; G06F 19/321; G06F 19/3406; G06Q 50/22; G06Q 50/24
USPC ........................................ 348/333.02, 211.99
See application file for complete search history.

(56) References Cited

U.S. PATENT DOCUMENTS

| | | | | |
|---|---|---|---|---|
| 7,461,079 B2* | 12/2008 | Walker | ................ | G06F 19/322 |
| 7,499,048 B2* | 3/2009 | Sieracki | ................ | A61B 5/00 |
| | | | | 345/156 |
| 8,548,826 B2* | 10/2013 | Herbst | ................ | G06Q 10/10 |
| | | | | 705/3 |
| 8,655,053 B1* | 2/2014 | Hansen | ............ | G06Q 30/0241 |
| | | | | 382/154 |
| 8,934,687 B2* | 1/2015 | Li | ......................... | G06F 19/321 |
| | | | | 382/128 |
| 9,015,630 B2* | 4/2015 | Soffer | ................ | G06F 3/0482 |
| | | | | 382/128 |
| 9,078,565 B2* | 7/2015 | Profio | .................... | A61B 6/03 |

(Continued)

FOREIGN PATENT DOCUMENTS

| | | |
|---|---|---|
| CN | 101146177 A | 3/2008 |
| JP | H09-298678 A | 11/1997 |

(Continued)

*Primary Examiner* — Ngoc-Yen Vu
(74) *Attorney, Agent, or Firm* — Canon USA Inc., IP Division (57) ABSTRACT

An image capture apparatus includes an image capture instruction obtaining unit configured to obtain an image capture instruction that specifies a target portion of a subject, an image capture instruction display unit configured to display the image capture instruction in a chart indicating the subject displayed on a display screen, and a reception unit configured to receive an image capture command in a state in which the image capture instruction is displayed on the display screen.

19 Claims, 8 Drawing Sheets

(56) References Cited

U.S. PATENT DOCUMENTS

| | | | |
|---|---|---|---|
| 2003/0055686 A1* | 3/2003 | Satoh | G06F 19/322 |
| | | | 705/3 |
| 2004/0151358 A1* | 8/2004 | Yanagita | G06F 19/321 |
| | | | 382/132 |
| 2009/0192823 A1* | 7/2009 | Hawkins | G06F 19/321 |
| | | | 705/3 |
| 2010/0020917 A1* | 1/2010 | Gagliano | 378/4 |
| 2012/0162222 A1* | 6/2012 | Zaiki | A61B 6/463 |
| | | | 345/419 |
| 2014/0126770 A1* | 5/2014 | Odessky | G06F 19/321 |
| | | | 382/103 |
| 2014/0164968 A1* | 6/2014 | Aalami | G06F 19/321 |
| | | | 715/771 |

FOREIGN PATENT DOCUMENTS

| | | |
|---|---|---|
| JP | 2001-60239 A | 3/2001 |
| JP | 2001-299767 A | 10/2001 |
| JP | 2004-295841 A | 10/2004 |
| JP | 2005-000631 A | 1/2005 |
| JP | 2006-075416 A | 3/2006 |
| JP | 2012-157666 A | 8/2012 |

* cited by examiner

```
START
  ↓
INPUT IMAGE CAPTURE INSTRUCTION  — S201
  ↓
IMAGE CAPTURE  — S202
  ↓
DISPLAY RESULT OF IMAGE CAPTURE  — S203
  ↓
END
```

FIG. 3

| | | 300 |
|---|---|---|
| PATIENT BASIC INFORMATION | PATIENT NAME | TARO YAMADA |
| | PATIENT ID | D12345678 |
| | AGE | 55 |
| | GENDER | MALE |
| IMAGE CAPTURE INFORMATION | DOCTOR NAME | JIRO SATO |
| | METHOD FOR CAPTURING IMAGE | DIGITAL CAMERA |
| | TARGET PORTIONS | RIGHT ELBOW, LEFT ELBOW, RIGHT BUTTOCK, LEFT KNEE |
| | REMARKS | CANNOT STAND UP |

CATEGORY: WHOLE BODY

BODY CHART NAME: WHOLE BODY FRONT

BODY CHART NAME: WHOLE BODY BACK

502

CATEGORY: HEAD

BODY CHART NAME: HEAD FRONT

BODY CHART NAME: HEAD BACK

FIG. 6

| BODY CHART CATEGORY | NUMBER OF ELEMENTS | BODY CHART NAME | NUMBER OF ELEMENTS | ELEMENT (DISPLAYABLE PORTION) |
|---|---|---|---|---|
| WHOLE BODY | 45 | WHOLE BODY FRONT | 30 | {FRONT HEAD, ..., RIGHT ELBOW, ..., LEFT ELBOW, ...} |
|  |  | WHOLE BODY BACK | 15 | {BACK HEAD, ..., RIGHT SHOULDER BLADE, LEFT SHOULDER BLADE, BACK, WAIST, RIGHT BUTTOCK, LEFT BUTTOCK, ...} |
| HEAD | 20 | HEAD FRONT | 14 | {FRONT HEAD, RIGHT EYE SOCKET, LEFT EYE SOCKET, RIGHT EAR, LEFT EAR, NOSE, RIGHT CHEEK, LEFT CHEEK, ...} |
|  |  | HEAD BACK | 6 | {BACK HEAD, NECK BACK, RIGHT SHOULDER, LEFT SHOULDER, ...} |
| ⋮ |  | ⋮ |  |  |

IMAGE CAPTURE APPARATUS, IMAGE CAPTURE PROCESSING SYSTEM AND METHOD FOR PROCESSING IMAGE CAPTURE

BACKGROUND

Field of the Invention

Aspects of the present invention generally relate to an image capture apparatus, an image capture processing system, and a method for capturing an image.

Description of the Related Art

In these years, information is more and more digitized in medical institutions such as hospitals, and electronic medical records for managing diagnostic information regarding patients are being introduced. In the electronic medical records, diagnostic histories of patients, medication information, operation information, images of affected areas, X-ray images, and the like are managed in a unified manner, and data may be easily shared and reused. In addition, in accordance with recent increases in the capacity of storages, a large number of digital images of affected areas and the like may be captured and stored in the electronic medical records.

In such an environment, images of patients are often captured using digital cameras and the captured images are stored in the electronic medical records as clinical records. Especially in dermatology, surgery, and nursing, images of wounds, operative scars, and decubitus ulcers (bedsores) of patients are regularly captured using digital cameras, and changes in the affected areas over time are observed.

When the digital cameras are used in such a manner, doctors in charge do not necessarily capture images. It is possible that hospital photographers, nurses, or visiting nurses outside hospitals capture images in accordance with instructions from the doctors. In this case, the doctors need to provide basic information such as the names and identifiers (IDs) of target patients and image capture instructions including target portions and the number of images to be captured, and photographers need to capture images while referring to the instructions from the doctors.

In consideration of these circumstances, in Japanese Patent Laid-Open No. 2001-60239, a method for inputting a target portion of a patient is proposed in which a three-dimensional image of the patient is displayed on a screen when a doctor issues an image capture order and the order is easily issued when the doctor has directly specified the target portion in the displayed three-dimensional image.

In Japanese Patent Laid-Open No. 2001-60239, however, issuance of an image capture order by a doctor is described but how a photographer captures an image while referring to the image capture order is not described.

SUMMARY

Aspects of the present invention generally provide an image capture apparatus including an image capture instruction obtaining unit configured to obtain an image capture instruction that specifies a target portion of a subject, an image capture instruction display unit configured to display the image capture instruction in a chart indicating the subject displayed on a display screen, and a reception unit configured to receive an image capture command in a state in which the image capture instruction is displayed on the display screen.

Further features of the present disclosure will become apparent from the following description of exemplary embodiments with reference to the attached drawings.

DESCRIPTION OF THE EMBODIMENTS

Modes (embodiments) for implementing the present disclosure will be described hereinafter with reference to the drawings.

First Embodiment

It is assumed in a first embodiment that a photographer such as a visiting nurse or a care worker captures an image of a target patient, who is a subject, using a digital camera, which is an image capture apparatus, on the basis of an image capture instruction issued by a doctor.

Configuration of Image Capture Processing System

Figure 1:
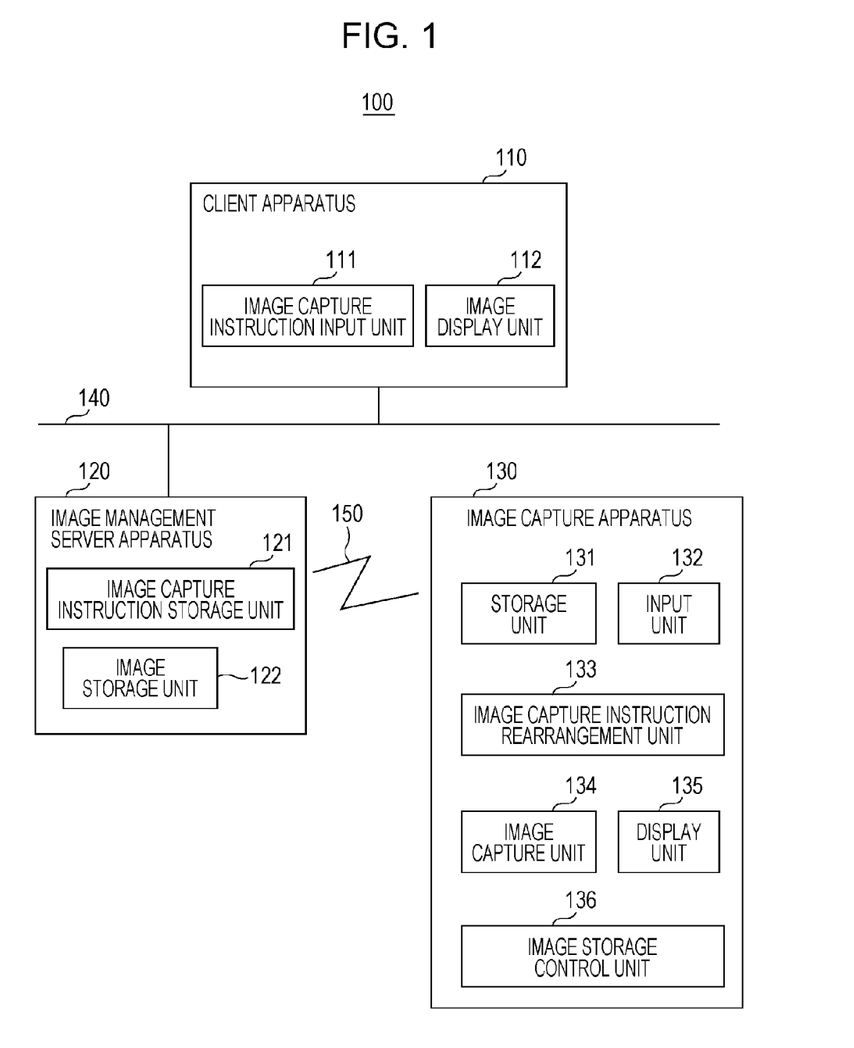
FIG. 1 is a diagram illustrating an example of the schematic configuration of an image capture processing system according to a first embodiment.

FIG. 1 is a diagram illustrating an example of the schematic configuration of an image capture processing system according to the first embodiment.

As illustrated in FIG. 1, an image capture processing system 100 according to this embodiment includes a client apparatus 110, an image management server apparatus 120, an image capture apparatus 130, a network 140, and a wireless network 150.

The client apparatus 110 and the image management server apparatus 120 are connected to each other through the network 140 in such a way as to be able to communicate with each other. The image management server apparatus 120 and the image capture apparatus 130 are connected to each other through the wireless network 150 in such a way as to be able to wirelessly communicate with each other.

The client apparatus 110 is an apparatus used by the doctor. The client apparatus 110 includes an image capture instruction input unit 111 and an image display unit 112. The image capture instruction input unit 111 is an input unit that enables the doctor to issue (input) an image capture order (image capture instruction). The image display unit 112 is a display unit that displays a captured image in order to enable the doctor to view the captured image.

The image management server apparatus 120 is an apparatus that manages a captured image. The image management server apparatus 120 includes an image capture instruction storage unit 121 and an image storage unit 122. The image capture instruction storage unit 121 is a storage unit that stores an image capture instruction input using the client apparatus 110 (image capture instruction input unit 111). The image storage unit 122 is a storage unit that stores an image captured by an image capture unit 134 of the image capture apparatus 130.

The image capture apparatus 130 is a camera (more specifically, a general-purpose camera) that captures an image of the target patient, who is the subject. The image capture apparatus 130 includes a storage unit 131, an input unit 132, an image capture instruction rearrangement unit 133, the image capture unit 134, a display unit 135, and an image storage control unit 136. The storage unit 131 is a storage unit that stores various pieces of information, various pieces of data, various tables, and the like. The input unit 132 is an input unit that enables the photographer to input various pieces of information, various instructions, and the like. The image capture instruction rearrangement unit 133 is a unit that rearranges image capture instructions input using the image capture instruction input unit 111 (image capture instructions stored in the image capture instruction storage unit 121). The image capture unit 134 is an image capture unit including an image capture sensor that converts an optical image of the subject obtained through an optical system such as a lens into an electronic image. The display unit 135 is a display unit including a liquid crystal display screen that displays a live preview and a captured image obtained from the image capture sensor of the image capture unit 134. The image storage control unit 136 is a control unit that performs control for storing images captured by the image capture unit 134 in the image storage unit 122 in accordance with order specified by image capture instructions input using the image capture instruction input unit 111 (image capture instructions stored in the image capture instruction storage unit 121).

The network 140 is a communication network that connects the client apparatus 110 and the image management server apparatus 120.

The wireless network 150 is a communication network that wirelessly connects the image management server apparatus 120 and the image capture apparatus 130.

Processing Procedure of Method for Processing Image Capture

Figure 2:
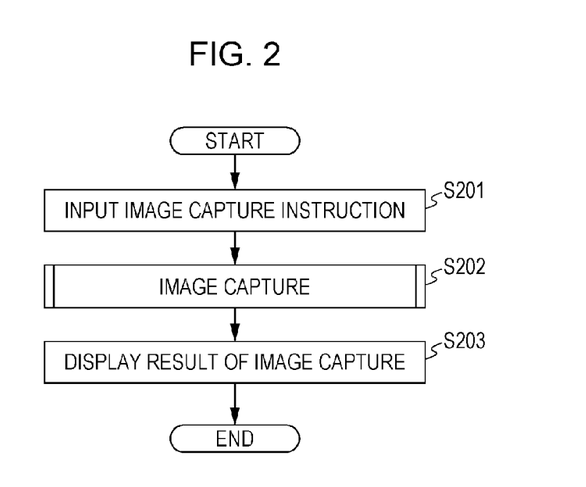
FIG. 2 is a flowchart illustrating an example of a processing procedure of a method for processing image capture used by the image capture processing system according to the first embodiment.

FIG. 2 is a flowchart illustrating an example of a processing procedure of a method for processing image capture used by the image capture processing system according to the first.

In S201, when the doctor has input an image capture instruction to the image capture instruction input unit 111, the client apparatus 110 receives the input image capture instruction. For example, the doctor inputs a target portion using the image capture instruction input unit 111. That is, the image capture instruction input unit 111 is an example of an image capture instruction input unit that inputs an image capture instruction including a target portion of a subject.

After receiving the image capture instruction, the client apparatus 110 transmits the image capture instruction to the image management server apparatus 120 through the network 140, and the image management server apparatus 120 stores the received image capture instruction in the image capture instruction storage unit 121. That is, a transmission unit included in the client apparatus 110 is an example of an image capture instruction transmission unit that transmits an image capture instruction to an image capture apparatus.

An example of the image capture instruction input by the doctor will be described later with reference to FIG. 3.

Next, in step S202, first, the image capture apparatus 130 reads (loads) image capture instructions from the image capture instruction storage unit 121 of the image management server apparatus 120 through the wireless network 150. For example, a processor or the like included in the image capture apparatus 130 reads the image capture instructions. Alternatively, the image capture apparatus 130 obtains the image capture instructions transmitted from the image management server apparatus 120 by receiving the image capture instructions using an interface unit included therein. That is, the processor or the interface unit included in the image capture apparatus 130 is an example of an image capture instruction obtaining unit that obtains an image capture instruction for specifying a target portion of a subject.

After obtaining the image capture instructions, the image capture apparatus 130 rearranges the image capture instructions and then displays the rearranged image capture instructions on the display unit 135. Thereafter, when the photographer captures images in accordance with the image capture instructions displayed on the display unit 135, the image capture apparatus 130 performs a process for capturing an image of the target patient. The image capture apparatus 130 then transmits the images of the target patient captured as a result of the process for capturing an image to the image management server apparatus 120 through the wireless network 150 to store the images in the image storage unit 122. Details of the processing procedure in step S202 will be described later with reference to FIG. 4.

Next, in step S203, the client apparatus 110 performs a process for displaying the captured images stored in the image storage unit 122 of the image management server apparatus 120 on the image display unit 112 in order to enable the doctor to view the captured images. At this time, the image display unit 112 displays the captured images in order in which the doctor has issued the corresponding image capture instructions. In this step, the client apparatus 110 displays the captured images stored in the image storage unit 122 of the image management server apparatus 120 on the image display unit 112 through the network 140 in such a way as to enable the doctor to view the captured images.

When the processing in step S203 has ended, the processing procedure illustrated in the flowchart of FIG. 2 ends.

Figure 3:
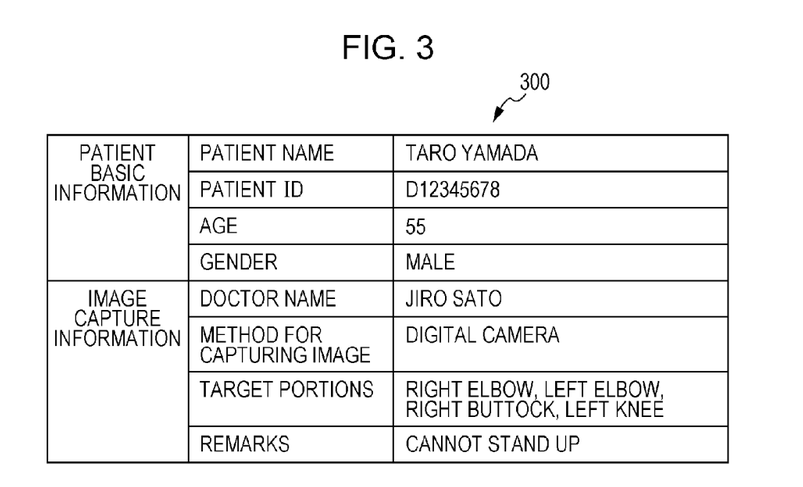
FIG. 3 is a schematic diagram illustrating an example of image capture instructions input by a doctor according to the first embodiment.

FIG. 3 is a schematic diagram illustrating an example of the image capture instructions input by the doctor according to the first embodiment.

As illustrated in FIG. 3, image capture instructions 300 include patient basis information regarding the target patient such as the name and ID of a patient, age, and gender and image capture information such as the name of a doctor, a method for capturing an image, target portions (target affected areas), and remarks. Although a plurality of target portions are simply described in the example illustrated in FIG. 3, details such as the number of images to be captured, an image capture angle, a reason for image capture, and remarks may be set for each target portion.

Process for Capturing Image

Figure 4:
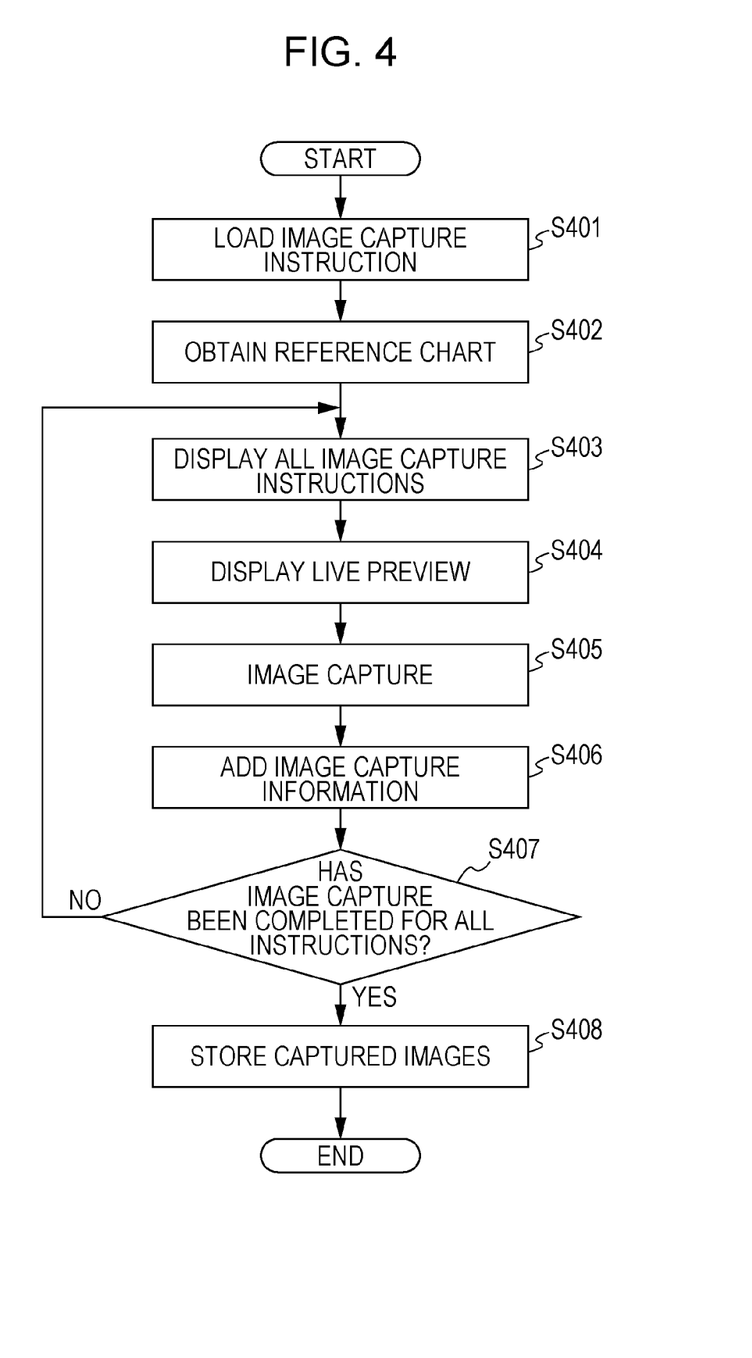
FIG. 4 is a flowchart illustrating an example of a detailed processing procedure of a process for capturing an image performed in step S202 illustrated in FIG. 2.

FIG. 4 is a flowchart illustrating an example of a detailed processing procedure of the process for capturing an image performed in step S202 illustrated in FIG. 2.

First, in step S401, the image capture apparatus 130 loads the image capture instructions stored in the image capture instruction storage unit 121 from the image management server apparatus 120 into, for example, the storage unit 131 through the wireless network 150. Here, the image management server apparatus 120 and the image capture apparatus 130 are connected to each other by the wireless network 150 such as short-range wireless communication typified by Bluetooth (registered trademark) or infrared communication.

Next, in step S402, the image capture apparatus 130 selects one of body charts (e.g. schemas) stored in the storage unit 131 that includes target portions loaded in step S401. That is, the processor included in the image capture apparatus 130 is an example of a body chart selection unit that selects a body chart including a target portion input using the image capture instruction input unit.

This step aims to automatically select an optimal body chart to be referred to upon which the image capture instructions are superimposed during image capture, and details will be described later with reference to FIGS. 5 to 7. Although the selection of a body chart in this step is performed by the image capture apparatus 130 in this embodiment, the image management server apparatus 120 may select a body chart and the selected body chart may be loaded as part of the image capture instructions loaded in step S401, instead.

Figure 8:
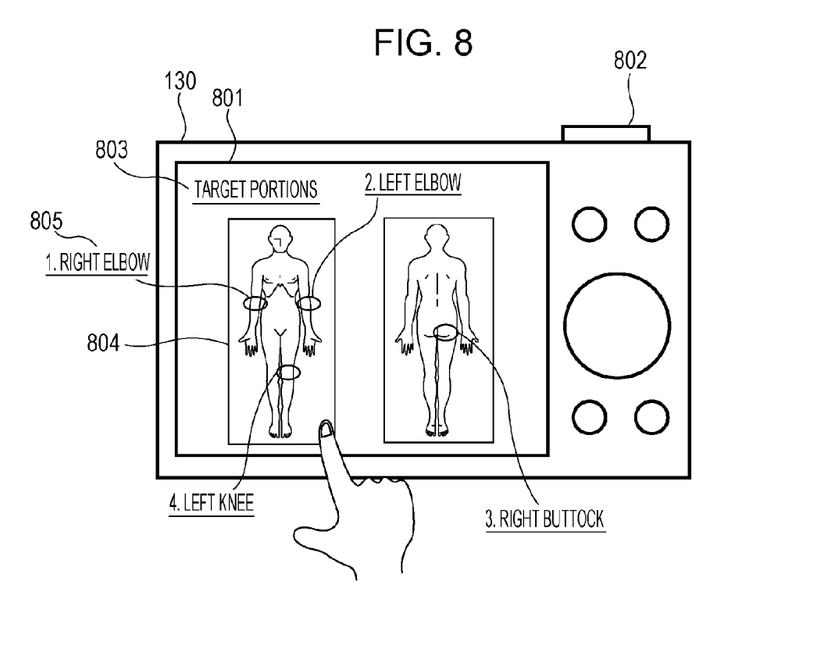
FIG. 8 is a schematic diagram illustrating an example of a user interface that displays all the image capture instructions in step S403 illustrated in FIG. 4.

Next, in step S403, the image capture apparatus 130 displays, on the display unit 135, the target portions whose images are to be captured. That is, a display control unit included in the image capture apparatus 130 displays, on the display unit 135, the target portions whose images are to be captured. Here, for example, all the target portions specified by the doctor are superimposed upon the body chart obtained in step S402 and displayed as illustrated in FIG. 8, which will be referred to later.

Next, when the photographer has selected one of the target portions displayed in step S402, the image capture apparatus 130 displays the image capture instruction regarding the selected target portion on the display unit 135 in step S404. When the display unit 135 has a touch panel function, one of the target portions may be selected using a touch panel, or may be selected using another operation unit (buttons or the like) included in the image capture apparatus 130. Upon receiving selection of one of the target portions by the doctor or the like, the processor included in the image capture apparatus 130 selects the target portion.

That is, the processor included in the image capture apparatus 130 is an example of a target portion selection unit that selects a target portion in a body chart displayed on a display unit of an image capture apparatus.

Figure 9:
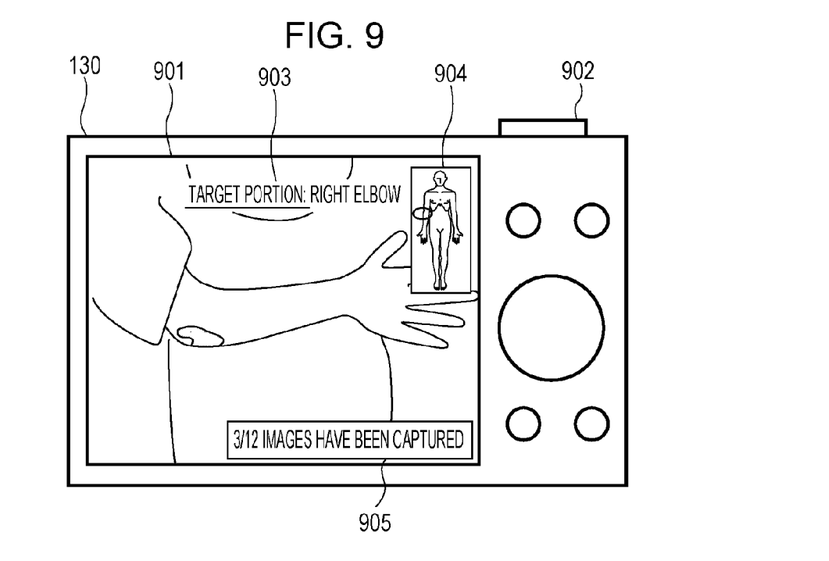
FIG. 9 is a schematic diagram illustrating an example of a user interface that displays an image capture instruction in step S404 illustrated in FIG. 4.

Here, for example, the image capture instruction is superimposed upon a live preview, which is a view from a viewfinder of the image capture apparatus 130, and displayed as illustrated in FIG. 9, which will be referred to later. That is, the display unit 135 is an example of an image capture instruction display unit that displays an image capture instruction in a chart indicating a subject. More specifically, the display unit 135 is an example of an image capture instruction display unit that displays a target portion in a body chart.

Next, when the photographer has pressed an image capture button, the image capture unit 134 of the image capture apparatus 130 performs the process for capturing an image, in which an image is captured by converting an optical image of the subject (target patient) obtained through the lens into an electronic image, in step S405. Here, the image capture button is an example of a reception unit that receives an image capture command in a state in which an image capture instruction is displayed on a display screen.

Next, in step S406, the image capture apparatus 130 (for example, the image capture unit 134) adds image capture information to the image captured in the process for capturing an image performed in step S405 as metadata. The image capture information to be added in this step includes not only information obtained during the image capture, such as a date and time of the image capture and a location of the image capture but also information obtained from the image capture instruction, such as the patient basic information regarding the target patient and the target portion. By adding the image capture information to the captured image, for example, the captured image may be searched for later by specifying a target portion using a keyword such as "right elbow". That is, the processor included in the image capture apparatus 130 records information regarding a target portion selected by the target portion selection unit while associating the information with a captured image.

Next, in step S407, the image capture apparatus 130 determines whether or not the image capture has been completed for all the image capture instructions.

If it is determined as a result of the determination made in step S407 that the image capture has not been completed for all the image capture instructions, the process returns to step S403. An image capture instruction for a target portion whose images is to be captured is displayed and the processing after step S403 is performed again.

On the other hand, if it is determined as a result of the determination in step S407 that the image capture has been completed for all the image capture instructions, the process proceeds to step S408.

In step S408, the image storage control unit 136 of the image capture apparatus 130 stores the images captured in the process for capturing an image performed in step S405 in the image storage unit 122 of the image management server apparatus 120 not in order in which the photographer has captured the images but in order of the target portions specified in the image capture instructions 300 illustrated in FIG. 3.

When the processing in step S408 has ended, the processing procedure illustrated in the flowchart of FIG. 4 ends.

Figure 5:
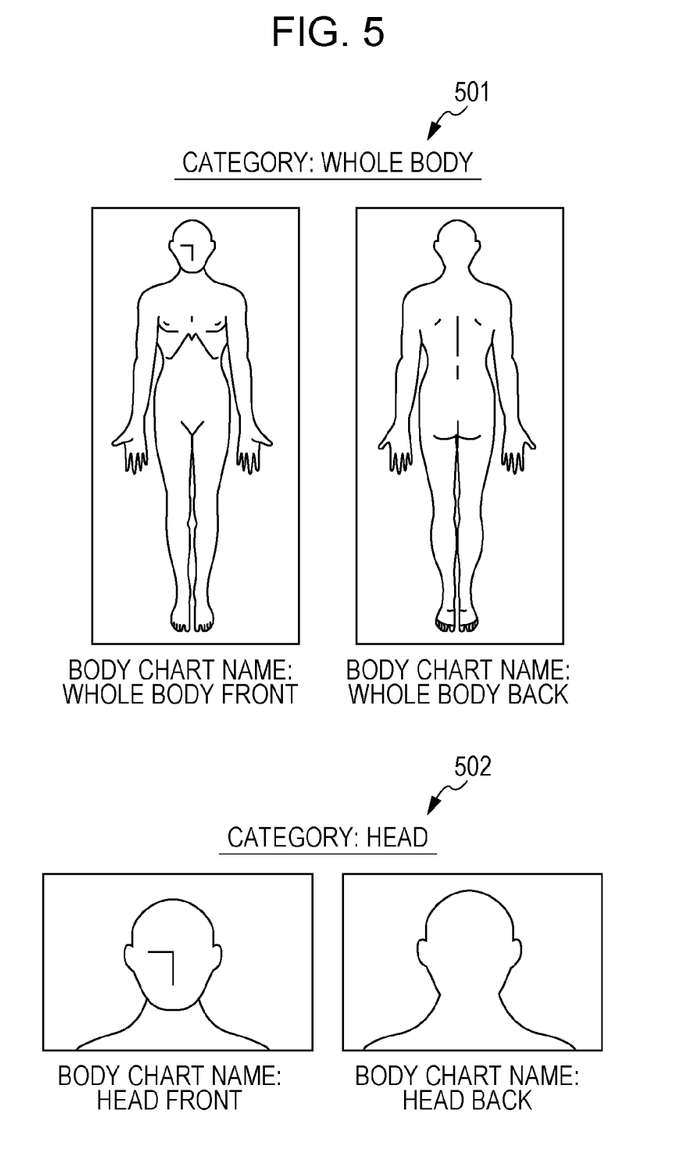
FIG. 5 is a schematic diagram illustrating an example of body charts for displaying the image capture instructions according to the first embodiment.
Figure 6:
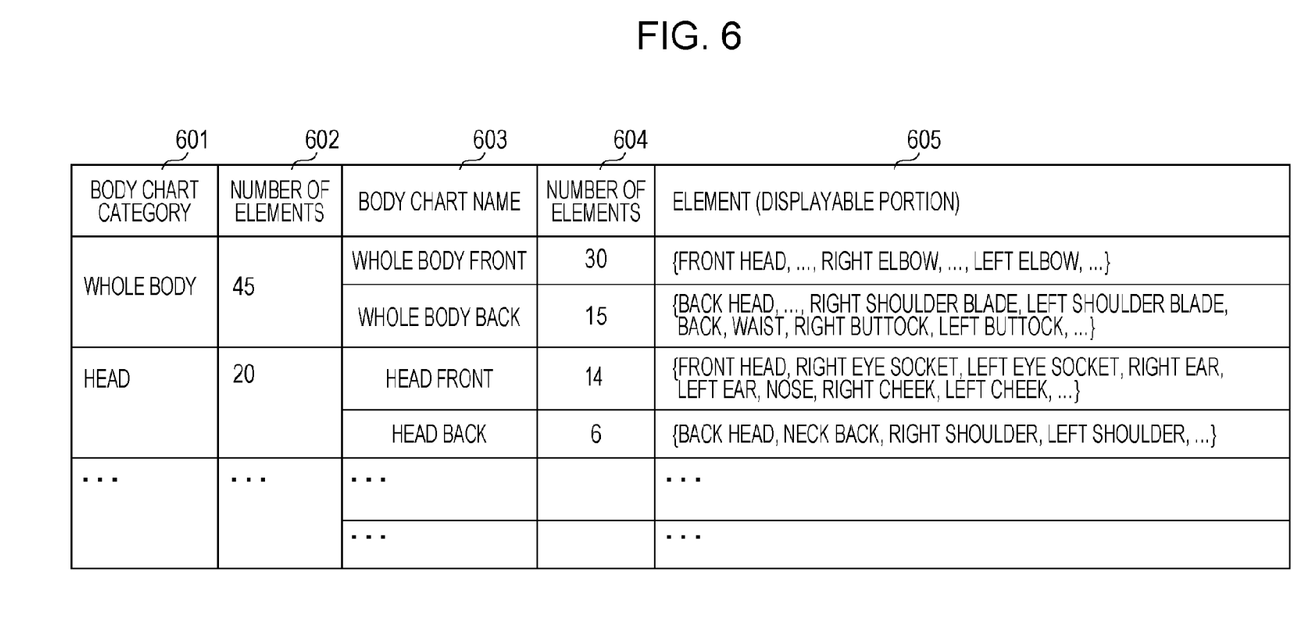
FIG. 6 is a schematic diagram illustrating a table representing relationships between body charts and displayable target portions according to the first embodiment.
Figure 7:
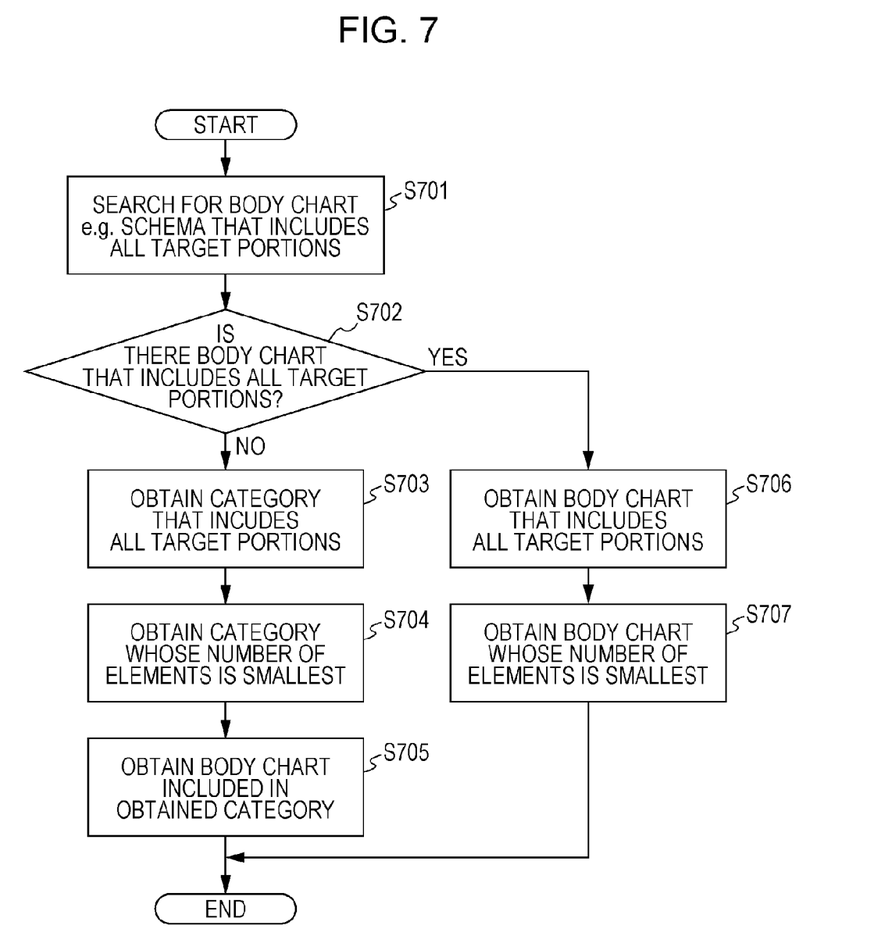
FIG. 7 is a flowchart illustrating details of a process for selecting a reference chart according to the first embodiment performed in step S402 illustrated in FIG. 4.

FIGS. 5 to 7 are schematic diagrams and a flowchart used in a process for selecting a reference chart according to the first embodiment performed in step S402 illustrated in FIG. 4.

FIG. 5 is a schematic diagram illustrating body charts that are candidates for a reference chart selected in step S402 illustrated in FIG. 4.

In FIG. 5, the image capture apparatus 130 holds a plurality of body charts. The body charts are provided with category names 501 and 502 indicating their respective display ranges of a human body, such as "whole body" and "head", and each category includes a body chart representing the front of a human body and a body chart representing the back of a human body. Although only "whole body" and "head" are illustrated here for convenience of description, other body charts that might be necessary depending on image capture circumstances, such as "right forearm" and "right palm", are prepared.

FIG. 6 is a schematic diagram illustrating a table used in the process for selecting a reference chart performed in step S402 illustrated in FIG. 4. The table illustrated in FIG. 6 is, for example, stored in the storage unit 131 of the image capture apparatus 130.

Body chart categories 601 are the category names 501 and 502 indicating the display ranges of a human body illustrated in FIG. 5. Each of the body chart categories 601 stores a body chart representing the front of a human body and a body chart representing the back of a human body in body chart names 603.

Elements 605 store the names of portions of a human body displayed in each of body charts indicated by the body chart names 603. The portions stored in the elements 605 need not necessarily be portions that may be accurately displayed in terms of the structure of a human body. For example, an element "right elbow" 605 included in a body chart name "whole body front" 603 should instead be included in a body chart name "whole body back" 603 in a strict sense, but because an image of the patient's right elbow is captured from the front while the patient is bending his/her right elbow as illustrated in FIG. 9, the element "right elbow" 605 is included in the body chart name "whole body front" 603 in order to enable the photographer to easily understand the display.

The number of elements 604 indicates the number of the elements 605 included in each of the body chart names 603, and the number of elements 602 indicates the number of the elements 605 included in each of the body chart categories 601. These numbers are used in calculation for selecting a reference chart performed in step S402 illustrated in FIG. 4.

FIG. 7 is a flowchart illustrating details of the process for selecting a reference chart performed in step S402 illustrated in FIG. 4.

First, in step S701, a body chart (e.g. schema) that includes all target portions is searched for.

Next, in step S702, whether or not there is a body chart that includes all the target portions is determined.

If it is determined as a result of the determination made in step S702 that there is a body chart that includes all the target portions, the process proceeds to step S706. On the other hand, it is determined as a result of the determination made in step S702 that there is no body chart that includes all the target portions, the process proceeds to step S703.

In step S703, a category that includes all the target portions is obtained. When it has been determined in step S702 that there is no body chart that includes all the target portions, it means that it is difficult to display all the instructions using only a body chart representing the front of a human body or a body chart representing the back of a human body. More specifically, for example, when the elements 605 illustrated in FIG. 6 are searched for the target portions "right elbow, left elbow, right buttock, left knee" illustrated in FIG. 3, there is no body chart that includes all the target portions since the right buttock is included only in the body chart representing the back of a human body and the left knee is included only in the body chart representing the front of the human body. Therefore, a search range is extended to the body chart categories 601, each of which includes both the body chart representing the front of a human body and the body chart representing the back of a human body.

In step S704, if a plurality of categories have been obtained in step S703, the numbers of elements 602 illustrated in FIG. 6 are referred to and a body chart category 601 having the smallest number of elements is obtained. This means that the smallest body chart that is capable of displaying all the instructions is obtained. In the case of the image capture instructions 300 illustrated in FIG. 3, only the body chart category "whole body" includes all the target portions "right elbow, left elbow, right buttock, left knee", and accordingly the body chart category "whole body" is obtained.

Next, in step S705, a body chart included in the category obtained in step S704 is obtained as a reference chart. In the example of the image capture instructions 300 illustrated in FIG. 3, body charts "whole body front" and "whole body back" are obtained.

When the processing in step S705 has been completed, the process illustrated in the flowchart of FIG. 7 ends.

Next, in step S706, if it is determined as a result of the determination made in step S702 that there is a body chart that includes all the target portions, the body chart is obtained. For example, when the target portions are "front head, right cheek", the elements 605 illustrated in FIG. 6 are searched and body charts "whole body front" and "head front", which include all the target portions, are obtained.

Next, in step S707, one of the body charts obtained in step S706 whose number of elements 604 illustrated in FIG. 6 is the smallest is obtained. By comparing the numbers of elements 604 of the body charts "whole body front" and "head front" obtained in step S706, the body chart "head front" whose number of elements 604 is smaller is obtained.

When the processing in step S707 has been completed, the process illustrated in the flowchart of FIG. 7 ends.

By this process, a body chart that includes all the target portions and that is most capable of displaying details of the target portions is obtained as a reference chart. That is, the processor included in the image capture apparatus 130 is an example of a body chart selection unit that automatically selects a body chart that includes target portions included in image capture instructions and that is most capable of displaying details of the target portions.

FIG. 8 is a schematic diagram illustrating an example of a user interface that displays all the target portions in step S403 illustrated in FIG. 4.

In FIG. 8, the image capture apparatus 130, which is a general-purpose digital camera, includes a liquid crystal display screen 801 and an image capture button 802. The liquid crystal display screen 801 is capable of receiving inputs through touch panel operations.

The liquid crystal display screen 801 includes the following display regions 803 to 805.

The display region 803 is a region indicating that a current screen is displaying target portions.

The display regions 804 is a region that displays an image capture instruction by superimposing the image capture instruction upon a body chart obtained by the process illustrated in FIG. 7. For example, the body charts "whole body front" and "whole body back" are obtained by the process illustrated in FIG. 7 for the image capture instructions 300 illustrated in FIG. 3, and displayed in the display region 804 as reference charts.

The display region 805 is a region that displays a target region in a body chart displayed in the display region 804. For example, the storage unit 131 of the image capture apparatus 130 stores a set of a plurality of body charts and combinations between coordinates in each of the plurality of body charts and portions as indices, and marks are provided at coordinates corresponding to target portions.

By touching the name of a target portion or a mark displayed in the display region 805, an image capture screen for the selected target portion is displayed as illustrated in FIG. 9.

FIG. 9 is a schematic diagram illustrating an example of the user interface that displays the live preview in step S404 illustrated in FIG. 4.

In FIG. 9, the image capture apparatus 130, which is a general-purpose digital camera, is provided with a liquid crystal display screen 901 and an image capture button 902.

The liquid crystal display screen 901 displays an image viewed from the lens as a live preview, and is capable of receiving inputs through touch panel operations.

When the photographer has pressed the image capture button 902, the image capture apparatus 130 performs the process for capturing an image in which an image is captured by converting an optical image of the subject (target patient) viewed from the lens into an electronic image.

The liquid crystal display screen 901 includes the following display regions 903 to 905.

The display region 903 is a region that displays a target portion whose image is to be captured by the photographer next time. A target portion selected in the display region 805 illustrated in FIG. 8 is displayed.

The display region 904 is a region that displays an image capture instruction relating to the target portion displayed in the display region 903 by superimposing the image capture instruction upon the body chart displayed in the display region 804 illustrated in FIG. 8. For example, the storage unit 131 of the image capture apparatus 130 stores a set of a plurality of body charts and combinations between coordinates in each of the plurality of body charts and target portions as indices, and marks are provided at coordinates corresponding to target portions. Only either the display region 903 or the display region 904 may be displayed, instead.

The display region 905 is a region that indicates the position of a current image capture instruction among all the image capture instructions.

When the image capture button 902 has been pressed and an image of a specified target portion has been captured, the number of images that have been captured increases.

The present disclosure is not limited to the example illustrated in FIG. 9, and, for example, information indicating an angle at which an image of the target patient is to be captured and information indicating a posture of the target patient in which an image is to be captured may be displayed, instead. These pieces of information may be indicated by characters or may be indicated by diagrams.

In addition, all of information indicating a target portion, information indicating the number of images to be captured, the information indicating an image capture angle, and the information indicating an image capture posture may be displayed, or an arbitrary piece of information may be selectively displayed. That is, the display unit 135 displays an image capture instruction including any or all of a target portion, the number of images to be captured, an image capture angle, and an image capture posture.

According to this embodiment, by displaying a body chart on the image capture apparatus 130 and superimposing an image capture instruction upon the body chart, the photographer who captures an image of a target patient using the image capture apparatus 130 may easily capture an image of a target portion included in the image capture instruction without an oversight.

In addition, as in step S406 illustrated in FIG. 4, by automatically adding metadata regarding a target portion to a captured image, an operation for inputting the target portion while checking the captured image may be omitted. Furthermore, the image may be searched for later using the target portion as a keyword.

Second Embodiment

A case in which a body chart is obtained in the process for obtaining a reference chart performed in step S402 illustrated in FIG. 4 and the body chart is displayed as a live preview while superimposing a target portion upon the body chart in step S404 has been described in the first embodiment. In a second embodiment, specification of image capture composition of a target portion is mainly focused upon, and an image of the same portion captured in the past is obtained as a reference image.

In the following description of the second embodiment, description of the same characteristics as those of the first embodiment is omitted, and only differences from the first embodiment will be described.

Figure 10:
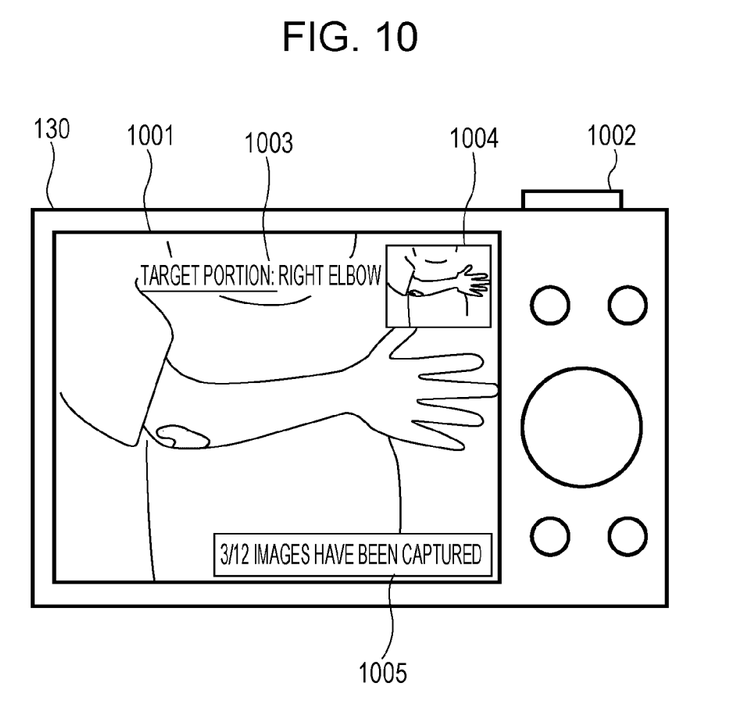
FIG. 10 is a schematic diagram illustrating an example of the user interface that displays an image capture instruction in step S404 illustrated in FIG. 4.

FIG. 10 is a schematic diagram illustrating an example of a user interface that displays the live preview in step S404 illustrated in FIG. 4.

An image capture apparatus 130, a display region 1001, an image capture button 1002, a display region 1003, and a display region 1005 are the same as the image capture apparatus 130, the display region 901, the image capture button 902, the display region 903, and the display region 905, respectively, illustrated in FIG. 9.

A display region 1004 displays an image including the same target portion as a target region displayed in the display region 1003. The image to be displayed may be searched for in the image storage unit 122 of the image management server apparatus 120 in the process for obtaining a reference chart performed in step S402 illustrated in FIG. 4 using the target portion displayed in the display region 1003 as a keyword and selected or, for example, when images of the same person are regularly captured as in the case of home-visit nursing, may be an image including the same portion of the patient as that included in an image captured in previous image capture. Alternatively, in the input of an image capture instruction in S201 illustrated in FIG. 2, the image capture instruction need not be input as a text but an image including the same portion as a target portion may be input as the image capture instruction. In this case, by extracting the name of the target portion from metadata regarding the image selected as the image capture instruction, the same processing as that according to the first embodiment may be performed thereafter.

According to this embodiment, by displaying an image captured in the past including the same portion as a target portion included in an image capture instruction on the image capture apparatus 130, the photographer who captures an image of a target patient using the image capture apparatus 130 may easily capture an image of the target portion without an oversight while referring to image capture composition included in the image capture instruction in which the image of the target portion is to be captured.

Other Embodiments

Additional embodiments can also be realized by a computer of a system or apparatus that reads out and executes computer executable instructions recorded on a storage medium (e.g., computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these embodiments are not seen to be limiting. The scope of the following claims is to be accorded the broadest interpretation so as to encompass all such modifications and equivalent structures and functions.

This application claims the benefit of Japanese Patent Application No. 2012-279484, filed Dec. 21, 2012, which is hereby incorporated by reference herein in its entirety.

What is claimed is:

1. An apparatus, having an image capturing unit, comprising:
at least one processor; and
at least one memory storing instructions that, when executed by the at least one processor, cause the apparatus to perform operations including:
obtaining an image capture order including information about one or a plurality of target portions of a subject, the one or the plurality of target portions corresponding to a portion of the subject to be captured;
displaying, on a display screen, a live view and a schema in which at least one target portion from among the one or the plurality of target portions corresponding to the information is displayed;
receiving an image capture command in a state in which the live view and the schema are displayed on the display screen; and
determining whether or not the image capture has been completed for all of the one or the plurality of target portions corresponding to the information.

2. The apparatus according to claim 1, wherein the subject is a human body.

3. The apparatus according to claim 1, wherein the displaying includes displaying an image capture order including any or all of the one or the plurality of target portions, a number of images to be captured, an image capture angle, and an image capture posture.

4. The apparatus according to claim 1, wherein the displaying includes displaying the schema in which the at least one target portion corresponding to the information is displayed smaller than the live view.

5. The apparatus according to claim 1, wherein the capturing includes capturing an image of the subject according to the received image capture command.

6. The apparatus according to claim 1, wherein the operations further include:
receiving selection for the at least one target portion from among the one or the plurality of target portions corresponding to the information included in the image capture order, and
wherein the displaying includes displaying, on the display screen, the live view and the schema in which the at least one target portion for which the selection is received by the receiving of the selection is displayed.

7. The apparatus according to claim 6,
wherein the displaying is capable of displaying a first screen for receiving selection for the at least one target portion by the receiving of the selection and a second screen for displaying the live view and the schema, and
wherein, in a case where it is determined, by the determining, that the image capture has not been completed for all of the one or the plurality of target portions corresponding to the information, the displaying includes switching a display from the second screen to the first screen after capturing of the at least one target portion for which the selection is received by the receiving of the selection has been performed according to the image capture command.

8. The apparatus according to claim 7,
wherein, in a case where it is determined, by the determining, that the image capture has been completed for all of the one or the plurality of target portions corresponding to the information, the displaying includes switching a display from the second screen to the first screen.

9. The apparatus according to claim 1,
wherein the displaying includes displaying the schema in such a manner that the schema is superimposed on the live view.

10. A control method for an apparatus having an image capturing unit, the control method comprising:
obtaining an image capture order including information about one or a plurality of target portions of a subject, the one or the plurality of target portions corresponding to a portion of the subject to be captured;
controlling a display unit to display, on a display screen, a live view of the subject and a schema in which at least one target portion from among the one or the plurality of target portions corresponding to the information is displayed;
receiving an image capture command in a state in which the live view and the schema are displayed on the display screen; and
determining whether or not the image capture has been completed for all of the one or the plurality of target portions corresponding to the information.

11. The control method according to claim 10 further comprising:
receiving selection for the at least one target portion from among the one or the plurality of target portions corresponding to the information included in the image capture order,
wherein the live view and the schema in which the at least one target portion for which the selection is received by the selection receiving unit is displayed on the display screen.

12. The control method according to claim 11,
wherein a first screen for receiving selection for the at least one target portion and a second screen for displaying the live view and the schema are displayed, and
wherein, in a case where it is determined that the image capture has not been completed for all of the one or the plurality of target portions corresponding to the information, a display is switched from the second screen to the first screen after capturing at least one of the target portion for which the selection is received has been performed according to the image capture command.

13. The control method according to claim 12,
wherein, in a case where it is determined that image capture has been completed for all of the one or the plurality of target portions corresponding to the information, the display is not switched from the second screen to the first screen.

14. The control method according to claim 10, wherein the schema is displayed in such a manner that the schema is superimposed on the live view.

15. A system, having an image capturing unit, comprising:
at least one processor; and
at least one memory storing instructions that, when executed by the at least one processor, cause the system to perform operations including:
obtaining an image capture order including information about one or a plurality of target portions of a subject, the one or the plurality of target portions corresponding to a portion of the subject to be captured;
displaying, on a display screen, a live view and a schema in which at least one target portion from among the one or the plurality of target portions corresponding to the information is displayed;
receiving an image capture command in a state in which the live view and the schema are displayed on the display screen; and
determining whether or not the image capture has been completed for all of the one or the plurality of target portions corresponding to the information.

16. The system according to claim 15, wherein the operations further include:
receiving selection for the at least one target portion from among the one or the plurality of target portions corresponding to the information included in the image capture order, and
wherein the displaying includes displaying, on the display screen, the live view and the schema in which the at least one target portion for which the selection is received by the receiving of the selection is displayed.

17. The system according to claim 16,
wherein the displaying is capable of displaying a first screen for receiving selection for the at least one target portion by the receiving of the selection and a second screen for displaying the live view and the schema, and
wherein, in a case where it is determined, by the determining, that the image capture has not been completed for all of the one or the plurality of target portions corresponding to the information, the displaying includes displaying switching a display from the second screen to the first screen after capturing of the at least one target portion for which the selection is received by the receiving of the selection has been performed according to the image capture command.

18. The system according to claim 17,
wherein, in a case where it is determined, by the determining, that the image capture has been completed for all of the one or the plurality of target portions corresponding to the information, the displaying does not include switching a display from the second screen to the first screen.

19. The system according to claim 15,
wherein the displaying includes displaying the schema in such a manner that the schema is superimposed on the live view.

* * * * *